United States Patent
Kim

(10) Patent No.: US 11,058,744 B2
(45) Date of Patent: Jul. 13, 2021

(54) COMPOSITION FOR TREATING PROSTATE CANCER

(71) Applicants: GemVax & KAEL Co., Ltd., Daejeon (KR); Sang Jae Kim, Seoul (KR)

(72) Inventor: Sang Jae Kim, Seoul (KR)

(73) Assignee: GemVax & KAEL Co., Ltd., Daejeon (KR)

(*) Notice: Subject to any disclaimer, the term of this patent is extended or adjusted under 35 U.S.C. 154(b) by 0 days.

(21) Appl. No.: 15/105,289

(22) PCT Filed: Dec. 17, 2014

(86) PCT No.: PCT/KR2014/012502
§ 371 (c)(1),
(2) Date: Jun. 16, 2016

(87) PCT Pub. No.: WO2015/093854
PCT Pub. Date: Jun. 25, 2015

(65) Prior Publication Data
US 2016/0375091 A1    Dec. 29, 2016

(30) Foreign Application Priority Data

Dec. 17, 2013  (KR) .................. 10-2013-0157456
Dec. 19, 2013  (KR) .................. 10-2013-0159571

(51) Int. Cl.
| A61K 38/10 | (2006.01) |
| A61K 45/06 | (2006.01) |
| A61K 38/19 | (2006.01) |
| A61K 31/337 | (2006.01) |
| C07K 7/08 | (2006.01) |

(52) U.S. Cl.
CPC ............ *A61K 38/10* (2013.01); *A61K 31/337* (2013.01); *A61K 38/193* (2013.01); *A61K 45/06* (2013.01); *C07K 7/08* (2013.01)

(58) Field of Classification Search
CPC .... A61K 38/10; A61K 31/337; A61K 38/193; A61K 45/06; A61K 2300/00; C07K 7/08; A61P 43/00; A61P 35/04; A61P 35/00
See application file for complete search history.

(56) References Cited

U.S. PATENT DOCUMENTS

| 6,967,211 | B2 | 11/2005 | Inoue |
| 7,030,211 | B1* | 4/2006 | Gaudernack ........... A61K 38/45 424/184.1 |
| 7,786,084 | B2 | 8/2010 | Benner et al. |
| 7,794,723 | B2 | 9/2010 | Gaudernack et al. |
| 8,828,403 | B2 | 9/2014 | Filaci et al. |
| 8,933,197 | B2 | 1/2015 | Bogin et al. |
| 9,023,987 | B2 | 5/2015 | Chung et al. |
| 9,540,419 | B2 | 1/2017 | Kim et al. |
| 9,572,858 | B2 | 2/2017 | Kim et al. |
| 9,937,240 | B2 | 4/2018 | Kim et al. |
| 10,039,811 | B2 | 8/2018 | Kim et al. |
| 2002/0042401 | A1 | 4/2002 | Ferguson et al. |
| 2003/0027769 | A1 | 2/2003 | Scialdone et al. |
| 2003/0143228 | A1 | 7/2003 | Chen et al. |
| 2006/0106196 | A1 | 5/2006 | Gaudernack et al. |
| 2007/0190561 | A1 | 8/2007 | Morin et al. |
| 2007/0238647 | A1* | 10/2007 | Bowen .................. A61K 38/09 424/133.1 |
| 2008/0025986 | A1 | 1/2008 | Ozes et al. |
| 2009/0136917 | A1 | 5/2009 | Szalay et al. |
| 2009/0186802 | A1 | 7/2009 | Alluis et al. |
| 2009/0215852 | A1 | 8/2009 | Bascomb et al. |
| 2010/0003229 | A1 | 1/2010 | Santos |
| 2011/0135692 | A1 | 6/2011 | Filaci et al. |
| 2011/0150873 | A1 | 6/2011 | Grainger |
| 2011/0183925 | A1 | 7/2011 | Sato et al. |
| 2012/0065124 | A1 | 3/2012 | Morishita et al. |
| 2012/0208755 | A1 | 8/2012 | Leung |
| 2012/0277290 | A1 | 11/2012 | Collard et al. |

(Continued)

FOREIGN PATENT DOCUMENTS

| CN | 1313773 A | 9/2001 |
| EP | 1020190 A3 | 10/2000 |

(Continued)

OTHER PUBLICATIONS

ClinicalTrials. Adjuvant Leuprolide With or Without Docetaxel in High Risk Prostate Cancer After Radical Prostatectomy, 5 pages. Jan. 26, 2006.*
Petrylak, Daniel. Rev. Urol. 8(Suppl 2): S48-S55, 2006.*
Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).
Tarantino, G., et al. "Spleen: a New Role for an Old Player?," World Journal of Gastroenterology, 17(33):3776-3784, Baishideng Publishing Group, United States (Sep. 2011).
Shay, J.W., and Keith, W.N., "Targeting Telomerase for Cancer Therapeutics," in: British Journal of Cancer 98(4):677-683, Nature Publishing Group on behalf of Cancer Research UK (2008).

(Continued)

*Primary Examiner* — Alana Harris Dent
(74) *Attorney, Agent, or Firm* — Clark & Elbing LLP; Susan M. Michaud

(57) ABSTRACT

The present invention relates to a composition for treating prostate cancer and, more specifically, to a composition for treating prostate cancer, which contains a peptide derived from telomerase and is effective in inhibiting growth and metastasis of prostate cancer cells. In addition, the present invention provides a composition and method for treating prostate cancer, wherein, when prostate cancer is treated, docetaxel and the peptide derived from telomerase are co-administered, thereby having a synergetic therapeutic effect compared with administration alone. Particularly, the present invention provides a treatment method useful for patients who do not have a sufficient anticancer effect merely through administration of docetaxel alone and patients who have hormone resistance.

16 Claims, 12 Drawing Sheets

Specification includes a Sequence Listing.

(56) References Cited

U.S. PATENT DOCUMENTS

| | | |
|---|---|---|
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |
| 2018/0036384 A1 | 2/2018 | Kim |
| 2018/0207241 A1 | 7/2018 | Kim |
| 2018/0318383 A1 | 11/2018 | Kim et al. |
| 2019/0030137 A1 | 1/2019 | Kim et al. |
| 2019/0032032 A1 | 1/2019 | Kim |
| 2019/0142894 A1 | 5/2019 | Kim et al. |

FOREIGN PATENT DOCUMENTS

| | | |
|---|---|---|
| EP | 1093381 B2 | 7/2009 |
| EP | 1817337 B1 | 1/2011 |
| JP | 2002520293 A | 7/2002 |
| JP | 2002522373 A | 7/2002 |
| JP | 2010252810 A | 11/2010 |
| JP | 2011515498 A | 5/2011 |
| JP | 2012500279 A | 1/2012 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20140104288 A | 8/2014 |
| WO | WO-0002581 A1 | 1/2000 |
| WO | WO-0007565 A2 | 2/2000 |
| WO | WO-2009025871 A1 | 2/2009 |
| WO | WO-2009120914 A1 | 10/2009 |
| WO | WO-2010003520 A2 | 1/2010 |
| WO | WO-2010012850 A1 | 2/2010 |
| WO | WO-2010022125 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167298 A1 | 11/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014046983 A1 | 3/2014 |
| WO | WO-2014130909 A1 | 8/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Co-pending Application, U.S. Appl. No. 15/772,928, inventors Kim, S.J., et al., filed on Nov. 3, 2016 (Not Published).

International Search Report and Written Opinion for International Application No. PCT/KR2016/012613, Korean intellectual Property Office, Republic of Korea, dated Feb. 2, 2017, 14 pages.

Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

Olney, J.W., et al., "Pathological Changes Induced in Cerebrocortical Neurons by Phencyclidine and Related Drugs," Science 244(4910):1360-1362, American Association for the Advancement of Science, United States (Jun. 1989).

Co-pending Application, U.S. Appl. No. 15/479,746, inventors Kim, S.J., et al., filed on Apr. 5, 2017 (Not Published).

ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.

Hormones in MeSH Database, National Center for Biotechnology Information, accessed at http://www.ncbi.nlm.nih.gov/mesh/68006728, last accessed on May 8, 2017, 3 pages.

Kyte, J.A., et al., "Telomerase Peptide Vaccination Combined with Temozolomide: A Clinical Trial in Stage IV Melanoma Patients," Clinical Cancer Research 17(13):4568-4580, The Association, United States (2011).

Mandal, A., "Types of Fibrosis," news-medical.net, accessed at http://www.news-medical.net/health/Types-of-Fibrosis.aspx, last accessed on Jul. 3, 2014, 3 pages.

Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (Jul. 2014).

Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Ireland Ltd., Ireland (2010).

(56) References Cited

OTHER PUBLICATIONS

Rosenbloom, J., et al., "Strategies for Anti-fibrotic Therapies," Biochimica et Biophysica Acta 1832(7):1088-1103, Elsevier B.V., Netherlands (2013).
Tisdale, M.J., "Catabolic Mediators of Cancer Cachexia," Current Opinion in Supportive and Palliative Care, 2(4):256-261, Lippincott Williams & Wilkins, United States (2008).
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Agarwal et al., "CCL11 (eotaxin-1): a new diagnostic serum marker for prostate cancer," The Prostate 73(6):573-581 (2013).
Notification of Reason for Refusal dated Dec. 28, 2020 for Korean Patent Application No. 10-2016-7017789, Kim et al., "Composition for Treating Prostate Cancer," filed Dec. 17, 2014 (12 pages).
Albini, A., et al., "Cancer Prevention by Targeting Angiogenesis," Nature reviews Clinical oncology 9(9):498-509, Nature Pub Group (2012).
Auerbach, R., et al., "Angiogenesis Assays: Problems and Pitfalls," Cancer Metastasis Reviews 19(1-2):167-172, Kluwer Academic, Netherlands (2000).
Berendsen, H.J., "A Glimpse of the Holy Grail?," Science 282(5389):642-643, American Association for the Advancement of Science, United States (1998).
De Araujo, J.G., et al,, "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Du, C., et al., "Conformational and Topological Requirements of Cell-permeable Peptide Function," The Journal of Peptide Research 51(3):235-243, Munksgaard, Denmark (1998).
Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).
Fontanes, V., et al., "A cell permeable peptide inhibits Hepatitis C Virus Replication by Sequestering IRES Transacting Factors," Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Search Report for Application No. PCT/KR2016/007192, dated Sep. 12, 2016, 12 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
Jain, R.K., "Barriers to Drug Delivery in Solid Tumors," Scientific American 271(1):58-65, Scientific American, Inc., United States (Jul. 1994).
Kalnins, A., et al., "Sequence of the Lacz Gene of *Escherichia coli*," The EMBO Journal 2(4):593-597, Wiley Blackwell, England (1983).
Kim, B.H., "Presbycusis: Review for its Environmental Risk Factors," Korean Journal of Otorhinolaryngology—Head and Neck Surgery 49(10):962-967, Korean Society of Otolaryngology—Head and Neck Surgery, Korea (2006).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Lee, S.A., et al., "A Telomerase-Derived Peptide Regulates Reactive Oxygen Species and Hepatitis C Virus RNA Replication in HCV-Infected Cells Via Heat Shock Protein 90," Biochemical and Biophysical Research Communications 471(1):156-162, Elsevier, United States (Feb. 2016).
Leem G., et al., "Immunotherapy in Pancreatic Cancer; the Road Less Traveled," Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).
Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL:http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival In Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Neoptolemos J.P., et al., "Predictive 1-20 Cytokine Biomarkers for Survival In Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Priya, S.G., et al., "Skin Tissue Engineering for Tissue Repair and Regeneration," Tissue Engineering. Part B, Reviews 14(1):105-118, Mary Ann Liebert, Inc., United States (2008).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.

(56) References Cited

OTHER PUBLICATIONS

Rowe-Rendleman, C. and Glickman, R.D., "Possible therapy for age-related macular degeneration using human telomerase," Brain Research Bulletin 62(6):549-553, Elsevier Science Inc., United States (2004).
Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
SIGMA Genosys, "Designing Custom Peptides," accessed at http://www.sigma-genosys.com/peptide_design.asp, Accessed on Dec. 16, 2004, 2 pages.
Supplemental European Search Report for Application No. EP14808179, dated Jan. 10, 2017, 13 pages.
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Voet, D. and Voet, J.G., "Abnormal Hemoglobins," in Biochemistry, 2nd Edition, Chapter 9, pp. 235-241, John Wiley & Sons, Inc., United States (1995).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
Altschul, S.F., et al., "Basic Local Alignment Search Tool," Journal of Molecular Biology 215(3):403-410, Elsevier, England (1990).
Beer, T.M., et al., "Phase II Study of Weekly Docetaxel in Symptomatic Androgen-independent Prostate Cancer," Annals of Oncology 12(9):1273-1279, Oxford University Press, England (2001).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Brunsvig, P.F., et al., "Telomerase Peptide Vaccination in NSCLC: A Phase II Trial in Stage III Patients Vaccinated after Chemoradiotherapy and An 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 8 pages.
Choi, S.G., "Recent Advances in Cancer Cachexia," Journal of Korean Oncology Nursing 11(1):20-25 (2011).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dementia from Merck Manual, accessed on Jul. 29, 2009, pp. 1-17.

Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood 117(14):3720-3732, American Society of Hematology, United States (2011).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Engineer, D.R. and Garcia, J.M., "Leptin in Anorexia and Cachexia Syndrome," International Journal of Peptides 2012:Article ID 287457, Hindawi Publishing Corporation, United States (2012).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2)195-206, Wiley, England (2009).
Henry, J.Y., et al., "Lenalidomide Enhances the Anti-prostate Cancer Activity of Docetaxel in vitro and in vivo," The Prostate 72(8):856-867, Wiley-Liss, United States (2012).
HSE, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.

(56) References Cited

OTHER PUBLICATIONS

International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2014/012502, Korean Intellectual Property Office, Republic of Korea, dated Mar. 11, 2015, 10 pages.
International Search Report for International Application No. PCT/KR2013/008459, Korean Intellectual Property Office, Republic of Korea, dated Dec. 23, 2013, 8 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kern, K.A. and Norton, J.A., "Cancer Cachexia," Journal of Parenteral and Enteral Nutrition 12(3):286-298, Sage Publications, United States (1988).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3)289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Mattson, M.P., "Pathways Towards and Away From Alzheimer's Disease," Nature 430(7000):631-639, Nature Publishing Group, England (2004).
Mcconnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).

(56) References Cited

OTHER PUBLICATIONS

Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8)1542-1550, Taylor & Francis, United States (2010).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Roubenoff, R., et al., "Adjuvant Arthritis as a Model of Inflammatory Cachexia," Arthritis and Rheumatism 40(3):534-539, Wiley-Blackwell, United States (1997).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al,, "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/005031, Korean Intellectual Property Office, Republic of Korea, dated Sep. 22, 2014, 7 pages.

(56) References Cited

OTHER PUBLICATIONS

Written Opinion for International Application No. PCT/KR2014/005508, Korean Intellectual Property Office, Republic of Korea, dated Oct. 14, 2014, 13 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/012502, Korean Intellectual Property Office, Republic of Korea, dated Mar. 11, 2015, 20 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Heldin, C.H., et al., "TGF-Beta Signalling from Cell Membrane to Nucleus through SMAD Proteins," Nature 390(6659):465-471, Nature Publishing Group, England (1997).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Search Report for International Application No. PCT/KR2014/004752, Korean Intellectual Property Office, Republic of Korea, dated Jan. 16, 2015, 10 pages.
International Search Report for International Application No. PCT/KR2015/003642, Korean Intellectual Property Office, Republic of Korea, dated Jul. 3, 2015, 8 pages.
Massague, J., "Tgf-Beta Signal Transduction," Annual Review of Biochemistry 67:753-791, Annual Reviews, United States (1998).
Song, J., et al., "Characterization and Fate of Telomerase-Expressing Epithelia during Kidney Repair," Journal of the American Society of Nephrology 22(12):2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2015/003642, Korean Intellectual Property Office, Republic of Korea, dated Jul. 3, 2015, 16 pages.
Yi, A., et al., "Radiation-Induced Complications after Breast Cancer Radiation Therapy: a Pictorial Review of Multimodality Imaging Findings," Korean Journal of Radiology 10(5):496-507,Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Co-pending U.S. Application, U.S. Appl. No. 15/346,870, inventors Kim, Sang Jae, filed on Nov. 9, 2016 (Not yet Published).
Eisenegger, C., et al., "The Role of Testosterone in Social Interaction," Trends in Cognitive Sciences 15(6)263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).
International Preliminary Report on Patentability for International Application No. PCT/KR2014/010035, Korean Intellectual Property Office, Republic of Korea, dated Apr. 26, 2016, 13 pages.
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Morishita, M., and Peppas, N.A., "Is the Oral Route Possible for Peptide and Protein Drug Delivery?," Drug Discovery Today 11(19-20):905-910, Elsevier Science Ltd., England (2006).
National Institute of Diabetes and Digestive and Kidney Diseases, "Prostate Enlargement: Benign Prostatic Hyperplasia," Updated Sep. 2014, 14 pages.
Sasada, A., et al., "A Case of Elderly Patient With Lung Cancer Efficiently Treated With Dendritic Cell Immunotherapy,"The 20th International Congress of Personalized Medicine, Conference Program and Abstracts, Personalized Medicine Universe (Japanese edition) 4(Supplement 1): 2 pages, May 24, 2015.
Shaw, V.E., et al., "Current Status of GV1001 and Other Telomerase Vaccination Strategies in the Treatment of Cancer," Expert Review of Vaccines 9(9)1007-1016, Taylor & Francis, England (2010).
Written Opinion for International Application No. PCT/KR2014/010035, Korean Intellectual Property Office, Republic of Korea, dated Feb. 2, 2015, 11 pages.
Godet, Y., et al., "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response," *Clinical Cancer Research 18*(10):2943-2953, American Association for Cancer Research Inc., United States (2012).

\* cited by examiner

Docetaxel 3 nM

Docetaxel 3 nM + Pep1 1 µM

Docetaxel 3 nM + Pep1 3 µM

Docetaxel 3 nM + Pep1 10 µM

Docetaxel 3 nM + Pep1 30 µM

COMPOSITION FOR TREATING PROSTATE CANCER

BACKGROUND OF THE INVENTION

Field of the Invention

The present disclosure relates to a composition for treating prostate cancer, and in particular, to a composition for treating prostate cancer which includes a telomerase-derived peptide and is effective for inhibiting the growth and metastasis of prostate cancer cells.

Background Art

Prostate cancer is a cancer that frequently develops in western males, and, in the United States of America, about one third of male cancer patients suffer from prostate cancer. Referring to the US statistics in 2008, about 190,000 new cases are reported annually, and above 15% thereof, that is, 29,000 patients, die of prostate cancer (Jemal et al, Cancer statistics, 58(2):71-96, 2008).

In Korea, the incidence rate of prostate cancer was 1.2% in 1989, but is rapidly increasing: 2.8% in 2001, 4.5% in 2005, and 10.7% in 2010. The change in the age-standardized incidence rate of major cancers is 13.2% from 1999 to 2007, only a second to thyroidal cancer. In the case of males, prostate cancer ranks $5^{th}$ in term of the cancer development frequency. Such a high position of prostate cancer may be due to westernized diet patterns (Cancer Center, cancer statistics, 2012).

Prostate cancer can be treated by hormone therapy, surgical treatment, radiation therapy, chemotherapy, or a combination thereof. Hormone therapy is to inhibit production of androgen that is associated with the growth of prostate cancer or a function of androgen. As a way to treat prostate cancer, a testicle, which produces male hormone, may be removed; luteinizing hormone releasing hormone (LHRH) analogue or estrogen preparation, which acts on hypophyseal to reduce androgen, may be administered; or anti-androgen preparations may be administered.

As a prostate cancer treatment, only hormone therapy is used. However, in most cases of advanced prostate cancer patients who experience hormone therapy, within several years, hormone tolerance occurs, and thus, it is difficult to continue treatments. Accordingly, there is a need to develop a method of treating prostate cancer being applicable even to patients having a tolerance to hormone therapy.

PRIOR ART

Patent Document (Patent Document 1) KR 2008-0084818

Non-Patent Document (Non-Patent Document 1) Jemal et al, Cancer statistics, 58(2):71-96, 2008

DETAILED DESCRIPTION OF THE INVENTION

Technical Problem

The inventors of the present application had made efforts to develop a method of effectively treating prostate cancer, and found that when a telomerase-derived peptide is administered alone or when the telomerase-derived peptide is co-administered with a conventional prostate cancer drug, such as docetaxel or leuprolide acetate, significant anti-cancer efficiency was able to be obtained, completing the present disclosure.

Accordingly, the present disclosure provides a composition for treating prostate cancer which inhibits the growth and metastasis of prostate cancer and a method of treating prostate cancer including administering the composition to a subject.

Technical Solution

An aspect of the present disclosure provides a composition for treating prostate cancer to be administered to a prostate cancer patient to inhibit the growth or metastasis of prostate cancer, the composition including a peptide having the amino acid sequence of SEQ ID NO: 1, a peptide having a sequence identity of at least 80% to the amino acid sequence, or a peptide fragment thereof.

In one embodiment, the composition may be co-administered with an anti-cancer drug.

In one embodiment, the anti-cancer drug may include docetaxel as a chemotherapeutic agent.

In one embodiment, the anti-cancer drug may include leuprolide acetate.

In one embodiment, the composition may be administered while being combined with an adjuvant.

In one embodiment, the adjuvant may include a cytokine adjuvant.

In one embodiment, the cytokine adjuvant may include a granulocyte-macrophage colony-stimulating factor (GM-CSF).

In one embodiment, the composition may be administered to a patient who has, at a serum level, the concentration (w/v) of at least one of eotaxin and MIP1α being at least 10% as high as average concentrations of eotaxin and MIP1α of patients including the patient.

In one embodiment, the composition may be co-used with leuprolide acetate that is an anti-cancer drug, and the adjuvant may be GM-CSF.

In one embodiment, the composition may be used to treat prostate cancer having hormone tolerance.

Another aspect of the present disclosure provides a kit for treating prostate cancer, the kit including: the composition for treating prostate cancer; and a manual.

In one embodiment, the manual may have a content that the composition for treating prostate cancer is co-administered with an anti-cancer drug selected from docetaxel and leuprolide acetate and is administered while being combined with an adjuvant, and the composition is administered to a patient who has, at a serum level, an eotaxin concentration (w/v) being at least 10% as high as an average eotaxin concentration of prostate cancer patients including the patient.

Another aspect of the present disclosure provides a method of treating prostate cancer to inhibit the growth or metastasis thereof in a prostate cancer patient, the method including administering the composition for treating prostate cancer to a subject that needs a treatment for prostate cancer.

Another aspect of the present disclosure provides a method of treating prostate cancer to inhibit the growth or metastasis thereof in a prostate cancer patient, the method including administering the composition for treating prostate cancer to a patient who has, at a serum level, an eotaxin concentration (w/v) being at least 10% as high as an average eotaxin concentration of prostate cancer patients including the patient.

Advantageous Effects of the Invention

According to the present disclosure, anti-cancer therapeutic effects may be improved by administering a telomerase-derived peptide to treat prostate cancer.

The present disclosure provides a composition and method of treating prostate cancer which provide higher synergic therapeutic effects by co-administering a telomerase-derived peptide with a conventional prostate cancer drug, such as docetaxel or leuprolide acetate, in treating prostate cancer. In particular, the present disclosure provides a therapeutic method that is useful for patients in which anti-cancer effects do not sufficiently occur when a conventional prostate cancer drug, such as docetaxel or leuprolide acetate, is administered alone, and patients having hormone tolerance.

DETAILED DESCRIPTION OF THE DRAWINGS/FIGURES

BEST MODE

Figure 1:
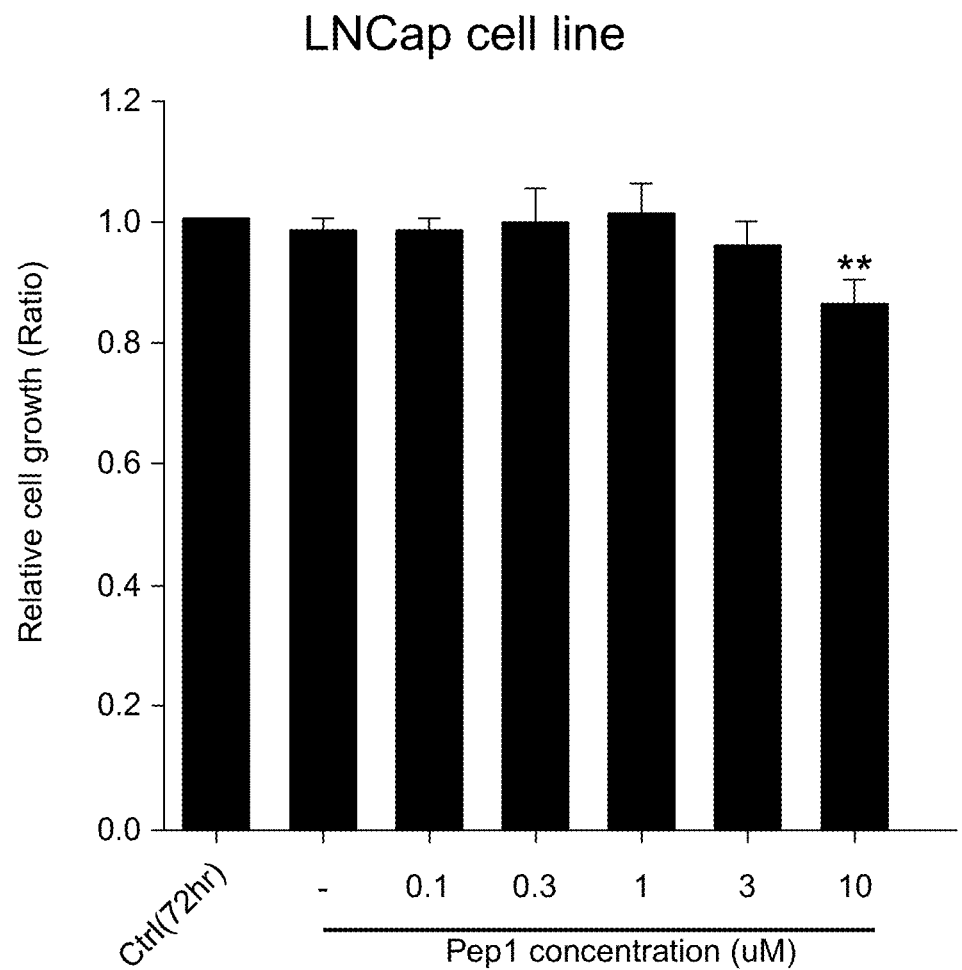
FIGS. 1 and 2 show graphs of relative cell growth with respect to Pep1 concentration obtained by MTT assay on a prostate cancer cell line (LNCaP) to identify cancer cells growth inhibition effects of a peptide including the amino acid sequence of SEQ ID NO: 1 ("Pep1").

Since the present disclosure can be adapted to various fields of use and in various modifications, the followings are more detailed descriptions of the present disclosure. Nevertheless, this is no means to limit the form of practical application; it should be understood that the intention is to include the concept and the extent of technology in all of the modifications, equivalents to alternatives. In describing the present disclosure, if any detailed description about the prior art is considered to deteriorate the fundamental principles of the present disclosure, the description will be omitted.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For example, cancer cells excrete an enzyme called telomerase, which prevents shortening of telomeres, thus resulting in proliferation of cancer cells. The inventors of the present application found that a telomerase-derived peptide is effective for the treatment of prostate cancer, thereby completing the present disclosure.

An aspect of the present disclosure provides a composition for treating prostate cancer including a telomerase-derived peptide, wherein the telomerase-derived peptide is a peptide derived from telomerase, for example, a peptide derived from Homo sapiens telomerase, and may be a peptide having a sequence of SEQ ID NO: 1 consisting of 16 amino acids (hereinafter referred to as 'Pep1') or a peptide having a sequence identity of at least 80% to the peptide sequence telomerase.

SEQ ID NO: 1: EARPALLTSRLRFIPK

In an embodiment of the present disclosure, a peptide of an amino acid sequence SEQ ID NO: 1, a peptide fragment of the above-mentioned peptide or a peptide having a sequence identity of 80% or greater to the amino acid sequence of the above-mentioned peptide comprise telomerase, in particular, telomerase derived from Homo sapiens was included.

The peptides disclosed herein may include peptides including an amino acid sequence at least 80%, at least 85%, at least 90%, at least 95%, at least 96%, at least 97%, at least 98%, at least 99% of sequence homology with the peptide of SEQ ID NO 1 or a fragment thereof. Moreover, the peptides disclosed in the present disclosure may include peptides having differences from SEQ ID NO: 1 or a fragment thereof in at least one amino acids, at least 2 amino acids, at least 3 amino acids, at least 4 amino acids, at least 5 amino acids, at least 6 amino acids, or at least 7 amino acids. In one embodiment, a peptide for inhibiting the proliferation of cancer cells may include 30 or less amino acids.

The peptide described in SEQ ID NO: 1 is same as the following table 1. The "name" in Table 2 below was for distinction of peptides. In one aspect, the peptide of SEQ ID NO:1 is the entire peptide of a human telomerase. In a different specific embodiment of the present disclosure, the peptide having a sequence of SEQ ID NO 1, the peptide which is a fragment of the peptide having the sequence of SEQ ID NO 1 or the peptide having 80% or more sequence identity with the peptide according to the present disclosure includes "synthetic peptides" synthesized by selecting and synthesizing a peptide corresponding to the pertinent position within the telomerase. SEQ ID NO: 2 is the amino acid sequence of the entire telomerase.

carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources.

TABLE 1

| SEQ ID No. | Name | PROSITION IN TELOMERASE | SEQUENCE | LENGTH |
|---|---|---|---|---|
| 1 | Pep1 | [611-626] | EARPALLTSRLRFIPK | 16 aa |
| 2 | | [1-1132] | MPRAPRCRAVRSLLRSHYREVLPLATFVRR LGPQGWRLVQRGDPAAFRALVAQCLVCVP WDARPPPAAPSFRQVSCLKELVARVLQRLC ERGAKNVLAFGFALLDGARGGPPEAFTTSV RSYLPNTVTDALRGSGAWGLLLRRVGDDV LVHLLARCALFVLVAPSCAYQVCGPPLYQL GAATQARPPPHASGPRRRLGCERAWNHSV REAGVPLGLPAPGARRRGGSASRSLPLPKRP RR GAAPEPERTPVGQGSWAHPGRTRGPSDRGF CVVSPARPAEEATSLEGALSGTRHSHPSVG RQHHAGPPSTSRPPRPWDTPCPPVYAETKH FLYSSGDKEQLRPSFLLSSLRPSLTGARRLV ETIFLGSRPWMPGTPRRLPRLPQRYWQMRP LFLELLGNHAQCPYGVLLKTHCPLRAAVTP AAGVCAREKPQGSVAAPEEEDTDPRRLVQL LRQHSSPWQVYGFVRACLRRLVPPGLWGS RHNERRFLRNTKKFISLGKHAKLSLQELTW KMSVRDCAWLRRSPGVGCVPAAEHRLREE ILAKFLHWLMSVYVVELLRSFFYVTETTFQ KNRLFFYRKSVWSKLQSIGIRQHLKRVQLR ELSEAEVRQHREARPALLTSRLRFIPKPDGL RPIVNMDYVVGARTFRREKRAERLTSRVKA LFSVLNYERARRPGLLGASVLGLDDIHRAW RTFVLRVRAQDPPPELYFVKVDVTGAYDTI PQDRLTEVIASIIKPQNTYCVRRYAVVQKA AHGHVRKAFKSHVSTLTDLQPYMRQFVAH LQETSPLRDAVVIEQSSSLNEASSGLFDVFL RFMCHHAVRIRGKSYVQCQGIPQGSILSTLL CSLCYGDMENKLFAGIRRDGLLLRLVDDFL LVTPHLTHAKTFLRTLVRGVPEYGCVVNLR KTVVNFPVEDEALGGTAFVQMPAHGLFPW CGLLLDTRTLEVQSDYSSYARTSIRASLTFN RGFKAGRNMRRKLFGVLRLKCHSLFLDLQ VNSLQTVCTNIYKILLLQAYRFHACVLQLPF HQQVWKNPTFFLRVISDTASLCYSILKAKN AGMSLGAKGAAGPLPSEAVQWLCHQAFLL KLTRHRVTYVPLLGSLRTAQTQLSRKLPGT TLTALEAAANPALPSDFKTILD | 1132 aa |

In one embodiment of the present disclosure, changes in amino acids include modifications of peptide's physical and chemical characteristics. For example, amino acid modification can be performed for improving thermal stability of the peptide, altering substrate specificity, and changing the optimal pH.

The term "amino acid" herein includes not only the 22 standard amino acids that are naturally integrated into a peptide but also the D-isomers and modified amino acids. Therefore, in a specific embodiment of the present disclosure, a peptide herein includes a peptide having D-amino acids. In addition, a peptide may include non-standard amino acids such as those that have been post-translationally modified. Examples of post-translational modification include phosphorylation, glycosylation, acylation(including acetylation, myristorylation, palmitoylation), alkylation, Meanwhile, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following Table 1:

TABLE 2

| Original amino acid | Examples of residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

The composition for treating the prostate cancer may include a peptide including an amino acid sequence of SEQ ID NO: 1, a peptide having a sequence identity of at least 80% to the amino acid sequence, or a peptide fragment thereof, in a concentration of 0.01 g/L to 1 kg/L, 0.1 g/L to 100 g/L, or 1 g/L to 10 g/L.

The dose, administration method, and administration interval of a peptide as used herein are already known in the art. Accordingly, according to the state of the patient, the patient may be treated by taking into consideration references known in the art. The dose may be within the range one of ordinary skill in the art may consider. For example, a dose per day may be in a range of 0.1 ng/kg/day to 10 mg/kg/day, or 0.1 µg/day to 1 mg/kg/day, or 1 µg/kg/day to 100 µg/kg/day, or 2 µg/kg/day to 50 µg/kg/day, but is not limited thereto. The dose per day may depend on various factors including, for example, the age, health status, or complications of a subject to which the peptide is to be administered.

In one embodiment, the peptides may be intracutaneously administered. The administration interval may be once per day at two-day intervals, and over time, the administration interval may be widened. During a first week, the administration may be performed three times per week ($1^{st}$, $3^{rd}$ and $5^{th}$ day), and during second, third, fourth, and sixth weeks, the administration may be performed once per week ($8^{th}$, $15^{th}$, $22^{nd}$, and $36^{th}$ day). Thereafter, every fourth week, the administration may be performed once per week. With respect to adults, the dose may be in a range of 0.1 to 3 mg. In one or more embodiments, the dose may be at least 0.1 mg, at least 0.2 mg, at least 0.3 mg, at least 0.4 mg, at least 0.45 mg, or at least 0.5 mg. In one or more embodiments, the dose may be at most 3 mg, at most 2.5 mg, at most 2.0 mg, at most 1.5 mg, at most 1.0 mg, at most 0.9 mg, at most 0.8 mg, at most 0.7 mg, or at most 0.6 mg.

Another aspect of the present disclosure provides a composition for treating prostate cancer, the composition including a peptide having the amino acid sequence of SEQ ID NO: 1, a peptide having a sequence identity of at least 80% to the amino acid sequence, or a peptide fragment thereof; and, as an active ingredient, docetaxel or leuprolide acetate, which are conventional prostate cancer drugs.

Docetaxel is an anti-cancer drug classified as "taxene", "antimicrotubule agent", or "plant alkaloids", and inhibits the growth of cancer cells by interrupting separation of microtubule, which is a structure for division and self-cloning during cell division.

Leuprolide is a hormone-blocking prostate cancer drug, classified as Leuprolide acetate, "Leuprorellin", or "LeuplinR". Leuprolide is a peptide classified as a gonadotropic hormone-releasing hormone agonist and includes 9 amino acids. Leuprolide has an activity being tens of times as strong activity as gonadotropic hormone in vivo, and, accordingly, strongly binds to a receptor thereof, thereby stopping any reaction of the receptor, leading to inhibiting secretion of sex hormone, such as testosterone.

Docetaxel is used to treat prostate cancer having a hormone tolerance. The treatment efficiency of docetaxel on the prostate cancer having a hormone tolerance is reported to be about 40% (Beer et al, Ann Oncol., 12:1273-1279, 2001). The dose of docetaxel varies depending on a patient. For example, the dose of docetaxel may be in a range of 60 to 400 mg/m². In general, docetaxel may be intravenously administered every three weeks in a dose of 60 to 100 mg/m² during 1 hour (France Cavelli at al, Textbook of Medical Oncology, Martin Dunitz Ltd., p4623(1997)).

Currently, the Food and Drug Administration (FDA) approves, for the prostate cancer treatment purpose, the use of docetaxel alone or a prednisolone combination use to reduce side effects. However, to treat intractable prostate cancer, there is a need to combine anti-cancer drugs having different mechanisms.

For example, there is a report that when rapamycin, which is an mTOR inhibitor, is used together with docetaxel, the growth of various prostate cancer is efficiently inhibited, and when lenalidomide, which is a thalidomide analogue, is administered together, anti-cancer effects are significantly increased (Liu et al, Chin Med J (Engl), 123(3):356-60, 2010; Henly et al. Prostate, 72(8):856-67, 2012).

When the peptides of the composition for treating prostate cancer according to an embodiment are used together with an anti-cancer drug, the peptide having the amino acid sequence of SEQ ID NO: 1, the peptide having a sequence identity of at least 80% to the amino acid sequence, or the peptide fragment thereof may be in an amount of 0.01 g/L to 1 kg/L, 0.1 g/L to 100 g/L, or 1 g/L to 10 g/L, and docetaxel may be in an amount of 0.01 ng/mL to 100 mg/mL, 0.1 ng/mL to 10 mg/mL, or 1 ng/mL to 1 mg/mL. However, these amounts may be appropriately adjusted when effects differ depending on a dose. Within these ranges or less or lower than the lower limits of the ranges, intended effects according to the present disclosure may be obtained, and stability and safety of the composition may be satisfied, and appropriate effects may be obtained even when costs are taken into consideration.

The peptides according to embodiments and/or an anti-cancer drug may be administered in combination with an adjuvant. In an immunologic aspect, an adjuvant is added to a vaccine to stimulate immunologic reactions with respect to a target antigen. The adjuvant, however, does not provide immunogenicity. Other than the adjuvant that stimulates immunologic reactions, there are adjuvants which are used to stabilize the formulation of a vaccine. Immunologic adjuvants are well known in the art [J Biomed Biotechnol. 2012; 2012: 831486. Published online Mar. 13, 2012]. An immunologic adjuvant includes an inorganic adjuvant, such as aluminum salt, and an organic adjuvant, such as oil, virosome, or squalane. Examples of the organic adjuvant include emulsion, microorganism-derived, synthetic adjuvant, cytokine, etc., but are not limited thereto. There are 9 kinds of cytokine adjuvants. Examples of cytokine adjuvant include adult granulocyte and a granulocyte-macrophage colony-stimulating factor (GM-CSF), which may activate macrophage. These cytokine adjuvants may be used in vaccines for B-type hepatitis, HIV, and cancer [J Biomed Biotechnol. 2012; 2012: 831486. Published online Mar. 13, 2012].

Doses of the adjuvants described above may be known in the art, and may be appropriately administered to a patient depending to the status of the patient by taking into consideration dose references known in the art. The doses may be within the ranges one of ordinary skill in the art may consider. The doses thereof per day may be in a range of 1 µg/kg/day to 10 g/kg/day, 10 µg/kg/day to 100 mg/kg/day, or 50 µg/kg/day to 10 mg/kg/day, but are not limited thereto. The doses may depend on various factors including, for example, the age, health status, or complications of a subject to which the adjuvants are to be administered.

For example, in the case of GM-CSF, GM-CSF may be administered, for example, in the adult-dose of 7 to 700 mg, 1 minute to 150 minutes, 5 minutes to 80 minutes, or 10 to 15 minutes, before the peptides according to embodiments are administered. In one or more embodiments, GM-CSF may be administered at least 1 minute, at least 3 minutes, at least 5 minutes, at least 7 minutes, at least 8 minutes, at least 9 minutes, or at least 10 minutes, before the peptides according to embodiments are administered. In one or more embodiments, GM-CSF may be administered at most 150 minutes at most 130 minutes, at most 110 minutes, at most 100 minutes, at most 90 minutes, at most 80 minutes, at most 70 minutes, at most 60 minutes, at most 50 minutes, at most 40 minutes, at most 30 minutes, at most 20 minutes, or at most 15 minutes, before the peptides according to embodiments are administered. In one or more embodiments, the dose may be at least 7 mg, at least 10 mg, at least 20 mg, at least 30 mg, at least 40 mg, at least 50 mg, at least 60 mg, or at least 70 mg. In one or more embodiments, the dose may be at most 700 mg, at most 600 mg, at most 500 mg, at most 400 mg, at most 300 mg, at most 200 mg, at most 100 mg, at most 90 mg, or at most 80 mg.

The composition according to one embodiment of the present disclosure may have applications with all animals including human, dog, chicken, pig, cow, sheep, guinea pig, and monkey.

An aspect of the present disclosure provides a pharmaceutical composition for inhibiting cancer cells growth, including, as an active ingredient, a peptide having the amino acid sequence of SEQ ID NO: 1, a peptide having a sequence identity of at least 80% to the amino acid sequence, or a peptide fragment thereof. The pharmaceutical composition according to an embodiment may be administered through oral, rectal, transdermal, intravenous, intramuscular, intraperitoneal, in the bone marrow, intradural, or subcutaneous routes.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

The pharmaceutical composition according to one embodiment of the present disclosure, if necessary, may contain additives, such as diluents, excipients, lubricants, binders, disintegrants, buffers, dispersants, surfactants, coloring agents, aromatics or sweeteners. In one embodiment of the present disclosure, the pharmaceutical composition may be manufactured by conventional methods of the industry in the art.

An aspect of the present disclosure provides a method of treating cancer, the method including using serum and plasma levels of cytokine of eotaxin, MIP1α and CRP as a biomarker that is used to determine whether an immunologic treatment is used in treating cancer. At a serum level, when a concentration (w/v) of one of eotaxin and MIP1α is at least 10% as high as average concentrations of eotaxin and MIP1α of patients having identical disease, the immunologic treatment may be performed. In one or more embodiments, when a serum eotaxin level is at least a predetermined level, for example, at least 20 pg/mL, at least 40 pg/ml, or at least 80 pg/ml, as high as an average serum eotaxin level of patients having identical disease, from among the patients, a patient having such a serum eotaxin level may selectively receive immunologic treatments together with existing anti-cancer treatment.

Mode

Hereinafter, the structure and effects of the present disclosure will be described by referring to Examples. However, the following examples are provided herein for illustrative purpose only and do not limit the scope of the present disclosure.

Example 1

Synthesis of Peptide and Preparation of Reagents and Cell Line

Synthesis of Peptide

A peptide of SEQ ID NO: 1 (hereinafter referred to as "Pep1") was prepared according to a solid phase peptide synthesis (SPPS) method known in the art. For example, peptides were synthesized by using ASP48S (Peptron, Inc., Daejeon, Korea) through Fmoc SPPS in such a manner that an amino acid was subjected to coupling in a direction from the C-terminus one by one. As below, in peptides, a resin is attached to the first amino acid of C-terminus. Examples of such peptides are as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin In the case of all amino acid materials used in synthesizing peptides, N-term was protected by Fmoc, and the residues were all protected by Trt, Boc, t-Bu (t-butylester), Pbf (2,2,4,6,7-pentamethyl dihydro-benzofuran-5-sulfonyl), etc. which are removable by an acid.

Examples thereof are as follows:
Fmoc-Ala-OH, Fmoc-Arg(Pbf)-OH, Fmoc-Glu(OtBu)-OH, Fmoc-Pro-OH, Fmoc-Leu-OH,
Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, and Trt-Mercaptoacetic acid.

As a coupling reagent, HBTU[2-(1H-Benzotriazole-1-yl)-1,1,3,3-tetamethylaminipM hexafluorophosphate]/HOBt

[N-Hydroxxybenzotriazole]/NMM [4-Methylmorpholine] was used. Fmoc was removed by using piperidine in 20% DMF. For the separation of synthesized peptides from resins and the removal of the protector from the residues, a cleavage cocktail [TFA (trifluoroacetic acid)/TIS (triisopropylsilane)/EDT (ethanedithiol)/$H_2O$=92.5/2.5/2.5/2.5] was used.

A starting amino acid with an amino acid protector binding thereto was bound to a solid support, and corresponding amino acids were allowed to react with the starting amino acid, followed by washing using a solvent and deprotection. By doing so, various peptides were synthesized. The synthesized peptides were cleaved from resins, and then, purified by using HPLC, and identified by MS and lyophilized. The purity level of all peptides used in experiments was at least 95%. The peptides were crystallized by high-performance liquid chromatography.

The peptide of SEQ ID NO: 1 (Pep1) was prepared as follows:

1) Coupling

An amino acid (8 e.q.) protected by NH2-Lys(Boc)-2-chloro-trityl resin and a coupling reagent HBTU(8 e.q.)/HOBt(8 e.q.)/NMM(16 e.q.) were dissolved in DMF, and the result was reacted at room temperature for 2 hours, followed by being sequentially washed with DMF, MeOH, and DMF in this state order.

2) Fmoc Deprotection

Piperidine in 20% DMF was added thereto, and then, the result was twice reacted at room temperature for 5 minutes, followed by being sequentially washed with DMF, MeOH, and DMF in this state order.

3) The processes 1) and 2) were repeatedly performed to obtain a peptide major skeleton: NH2-E(OtBu)-A-R(Pbf)-P-A-L-T(tBu)-S(tBu)-R(Pbf)L-R(Pbf)-F-I-P-K(Boc)-2-chloro-trityl resin.

4) Cleavage: cleavage cocktail was added to the completely synthesized peptide resin to separate the peptide from the resin.

5) The resultant mixture was mixed with cooling diethyl ether, and then centrifuged to precipitate the obtained peptide.

6) After purification by Prep-HPLC, a molecular amount of the result was identified by LC/MS. The result was lyophilized and prepared in powder.

2. Preparation of Reagents and Materials

Reagents and materials for use in experiments were prepared as follows: Pep1 prepared in powder was dissolved in 0.2 μm filtered steriled water, and then, stored after being aliquoted at a temperature of −70° C., and the aliquot was dissolved for use; docetaxel was dissolved in 100% EtOH, and mixed with tween 80 and PBS; 5-fluorouracil was dissolved in PBS; and leuprolide acetate was dissolved directly in PBS.

3. Preparation of Cell Line

An LNCaP cell line was used for experiments. The LNCaP cell line was a human prostate cancer metastasis cell, and obtained from American Type Cell Culture (ATCC, Rockville, Md.). The LNCaP cell line was incubated in a roswell park memorial institute medium (RPMI) containing 10% FBS(fetal bovine serum), 50 U/ml penicillin, and 50 μg/ml streptomycin until the cell population was 1 to $2 \times 10^6$/ml in a 5% $CO_2$ incubator in which the temperature was maintained at 37° C.

Example 2: Evaluating of cancer cell growth inhibition effects of Pep1 in LNCaP cell line model To identify effects of Pep1 on prostate cancer, the LNCaP cell line was subjected to MTT assay. The cancer cells growth inhibition effects were identified by using the reagents and materials and the cell line incubation method which are described in connection with Example 1. The MTT assay was performed as follows:

The LNCaP cell line having a certain cell population ($3 \times 10^3$/well) incubated in a 96 well plate (SPL) was incubated in a growth medium containing Pep1 (0, 0.1, 0.3, 1, 3, and 10 μM) and docetaxel (3 nM) for 72 hours, and MTT reagent was added in an amount of 40 μl to each well. After four hours of reaction, the cells were dissolved in DMSO, and an absorbance thereof was measured at a wavelength of 570 nm.

Separately, the same experiment as described above was performed, except that the incubation time and concentration of Pep1 varied. The LNCaP cell line having a certain cell population ($3 \times 10^3$/well) incubated in a 96 well plate (SPL) was cultured in a growth medium containing Pep1(0, 0.01, 1, 10, and 30 μM) for 96 hours, and then, the MTT reagent was added in an amount of 40 μl to each well. After four hours of reaction, the cells were dissolved in DMSO, and an absorbance thereof was measured at a wavelength of 570 nm.

To analyze test results, averages of test groups were verified by performing student's t-test. The reference of the statistical significance was set at $p<0.05$(*) or $p<0.01$(**).

Figure 2:
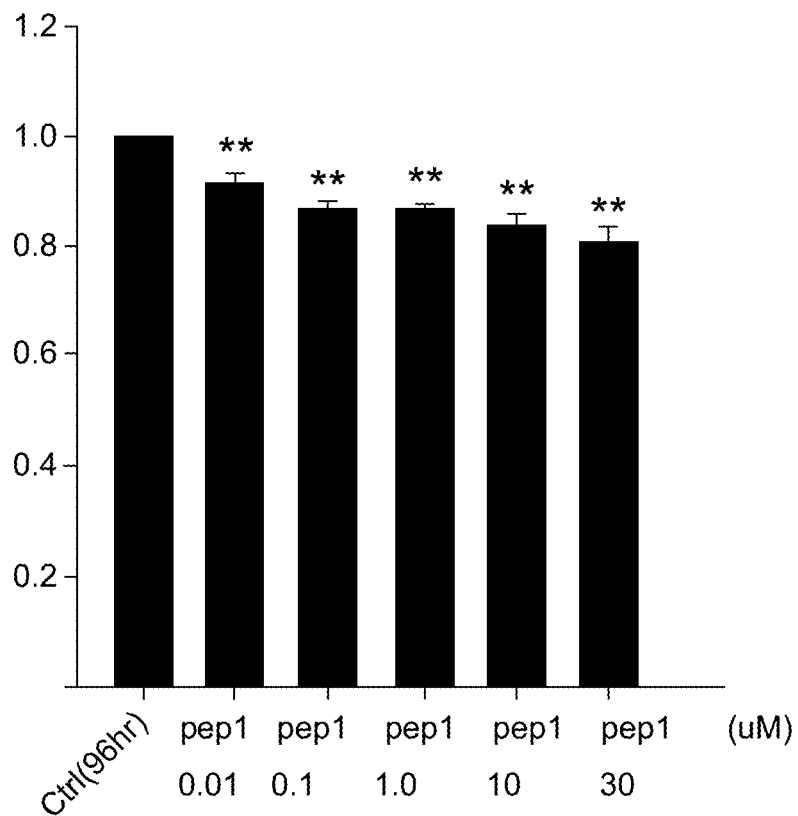

By performing the MTT assay as described above to identify cancer cells growth inhibition effects of Pep1 at various concentrations thereof, it was found that compared to the medium containing Pep1 having a concentration of 0 μM, 0.1 μM, 0.3 μM, 1 μM, or 3 μM, the medium containing Pep1 having a concentration of 10 μM showed statistically significant cell growth inhibition effects (see FIG. 1). The same experiment was further performed repeatedly, and the obtained test results also showed that Pep1 inhibited cell growth in a concentration-dependent manner (see FIG. 2).

Figure 3:
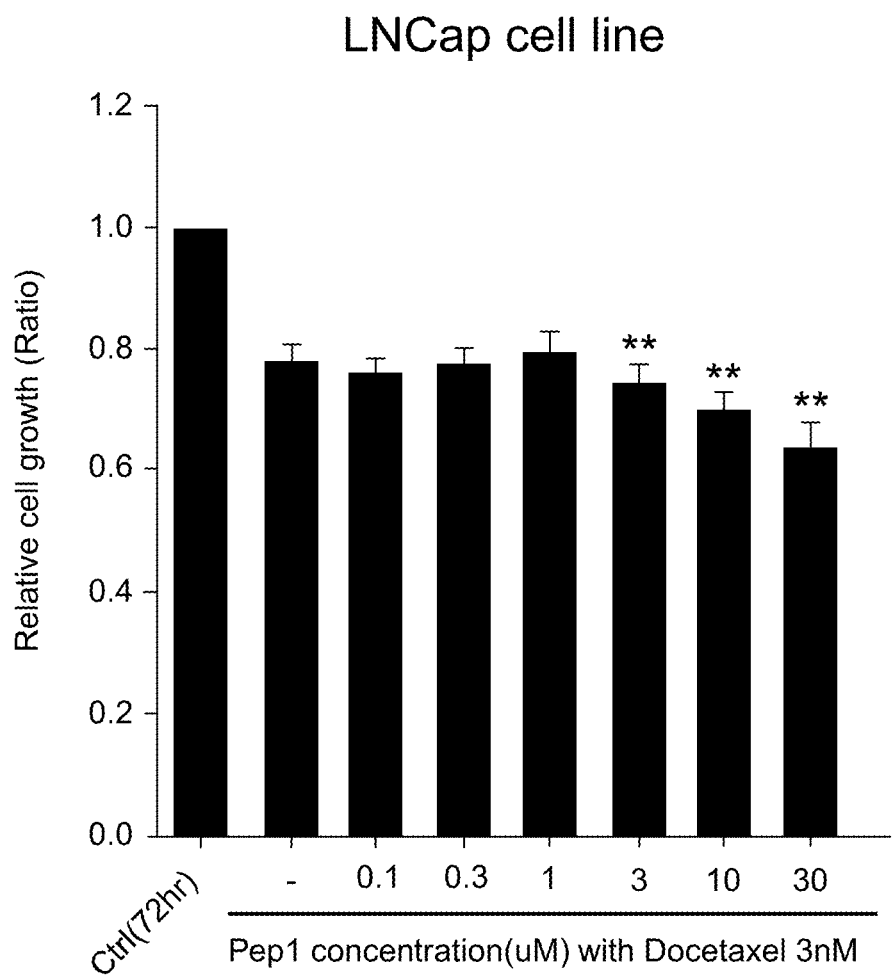
FIG. 3 shows a graph of relative cell growth obtained by MTT assay on an LNCaP to identify cancer cells growth inhibition effects when Pep1 is co-administered with docetaxel.

The MTT assay was performed on the medium containing 3 nM docetaxel and various concentrations of Pep1. The assay results also showed that compared to the medium containing 3 nM docetaxel and Pep1 having a concentration of 0 μM, 0.1 μM, 0.3 μM, or 1 μM, the medium containing 3 nM docetaxel and Pep1 having a concentration of 3 μM, 10 μM, or 30 μM showed statistically significant cell growth inhibition effects (see FIG. 3). This result shows that even when Pep1 is used together with docetaxel, Pep1 has concentration-dependent cell growth inhibition effects.

Example 3: Measuring the volume of cancer cells to which Pep1 was administered in LNCaP cell xenograft model This experiment was performed to confirm effects of Pep1 on the volume of cancer cells.

Test groups 1) to 7) were grafted with the LNCaP cell. This experiment was performed by using the reagents and materials and the cell line incubation method which are described in connection with Example 1.

The LNCaP cell line was a human prostate cancer metastasis cell, and obtained from American Type Cell Culture (ATCC, Rockville, MD). The LNCaP cell line was incubated in a roswell park memorial institute medium (RPMI) containing 10% FBS, 50 U/ml penicillin, and 50 μg/ml streptomycin until the cell population was 1 to $2 \times 10^6$/ml in a 5% $CO_2$ incubator in which the temperature was maintained at 37° C.

Test animals: 7 test groups were grafted with the LNCaP cell. The test groups consisted of 5-week BALB/c-nu mice (obtained from Central Lab. Animal Inc., Seoul, Korea). For each group, 6 mice and extra 5 mice were stabilized for 1 week. Each mouse was grafted at its side with the LNCaP cell having the cell population of 1*10⁷ cells suspended in 100 μl PBS, and observed for 2 weeks. From among the total of 11 mice, 5 mice that had not developed tumor or that had had a significantly small tumor were not used. The 7 test groups, each consisting of the remaining 6 mice, were treated according to the conditions as below for 20 days. Tumor volume was measured by using calipers according to the following:

[width$^2$×length×0.5 cm$^3$]

Following the grafting, Pep1 and leuprolide acetate (positive control) were administered to the 6 test groups by subcutaneous injection every day.
1) LNCaP-grafted control (vehicle)
2) LNCaP graft+0.01 mg/kg of Pep1
3) LNCaP graft+0.1 mg/kg of Pep1
4) LNCaP graft+1 mg/kg of Pep1
5) LNCaP graft+10 mg/kg of Pep1
6) LNCaP graft+0.1 mg/kg of leuprolide acetate
7) LNCaP graft+0.1 mg/kg of leuprolide acetate+0.1 mg/kg of Pep1

Additionally, effects of co-use of Pep1 and docetaxel on the volume of cancer cells were evaluated as follows:

Test groups 8) to 13) were grafted with the LNCaP cell. This experiment was performed by using the reagents and materials and the cell line incubation method which are described in connection with Example 1.

Test animals: 6 test groups were grafted with the LNCaP cell. The test groups consisted of 5-week BALB/c-nu mice (obtained from Central Lab. Animal Inc., Seoul, Korea). For each group, 6 mice and extra 5 mice were stabilized for 1 week. Each mouse was grafted at its side with the LNCaP cell having the cell population of 1*10⁷ cells suspended in 100 μl PBS, and observed for 2 weeks. From among the total of 11 mice, 5 mice that had not developed tumor or that had had a significantly small tumor were not used. The 7 test groups, each consisting of the remaining 6 mice, were treated according to the conditions as below for 20 days. Tumor volume was measured by using calipers according to the following:

[width×length×0.5 cm$^3$]

Following the grafting, Pep1 and docetaxel were administered to the 5 test groups
8) LNCaP-grafted control
9) LNCaP graft+20 mg/kg of docetaxel (once a week, intraperitoneal administration)
10) LNCaP graft+30 mg/kg of Pep1 (three times a week, subcutaneous administration)
11) LNCaP graft+3 mg/kg of Pep1+20 mg/kg of docetaxel
12) LNCaP graft+10 mg/kg of Pep1+20 mg/kg of docetaxel
13) LNCaP graft+30 mg/kg of Pep1+20 mg/kg of docetaxel Then, the amounts of water and diet, the tumor volume (a shorter diameter, a longer diameter), tumor weight/body weight, thigh muscle weight were measured. In addition, cancer cell samples were prepared, and PCNA (cell growth marker)/TUNEL (apoptosis marker) staining was performed.

To analyze test results, averages of test groups were verified by performing student's t-test. The reference of the statistical significance was set at p<0.05(*) or p<0.01(**).

Figure 4:
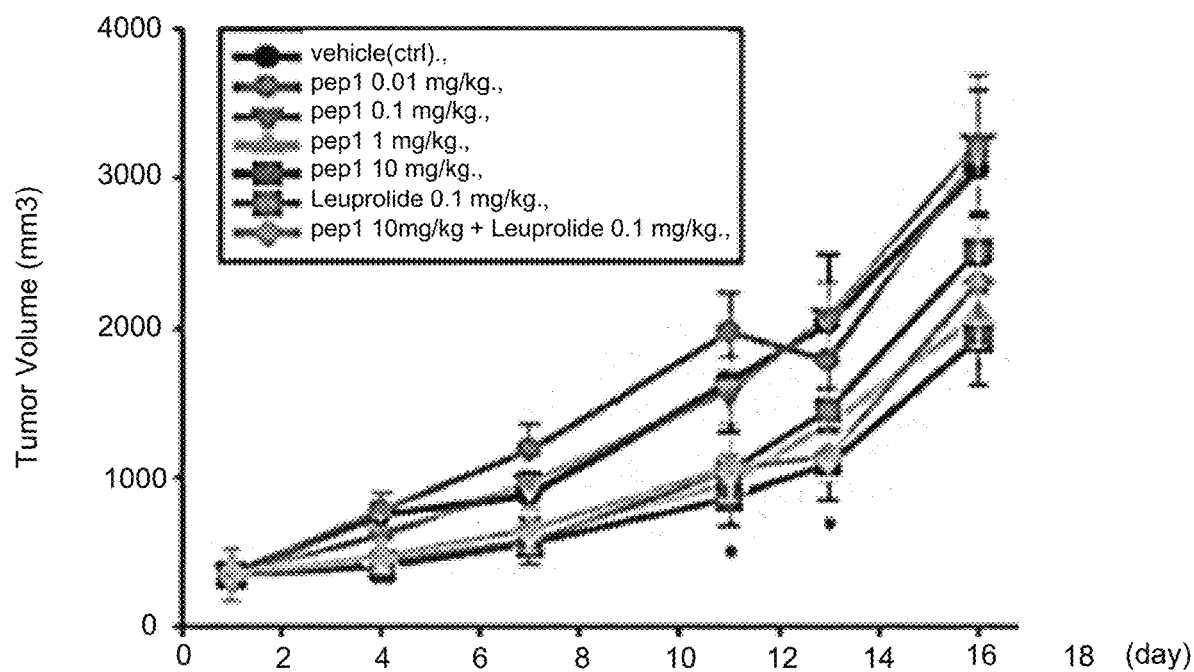
FIG. 4 shows a graph of tumor volume over time of test groups to which Pep1 and leuprolide acetate are administered separately or together, to evaluate efficacy of Pep1 and leuprolide acetate in an LNCaP cell-xenograft model.

Test results showed that when Pep1 was administered in a concentration of 0.01 mg/kg and 0.1 mg/kg, significant cancer growth inhibition effects were not obtained, but when Pep1 was administered in a concentration of 1 mg/kg and 10 mg/kg, compared to leuprolide acetate, which was a positive control, high inhibition effects were obtained (see FIG. 4, the Y axis of FIG. 4 indicates a tumor volume (mm$^3$)). That is, significant cancer growth inhibition effects of Pep1 on the LNCaP cell were identified even in an animal model. Referring to the test group 7) in which Pep1 was co-administered with leuprolide acetate and the test group 6) in which leuprolide acetate was administered alone, it is confirmed that even the co-administration of Pep1 and leuprolide acetate produces effects of inhibiting the volume of cancer cells.

Figure 5:
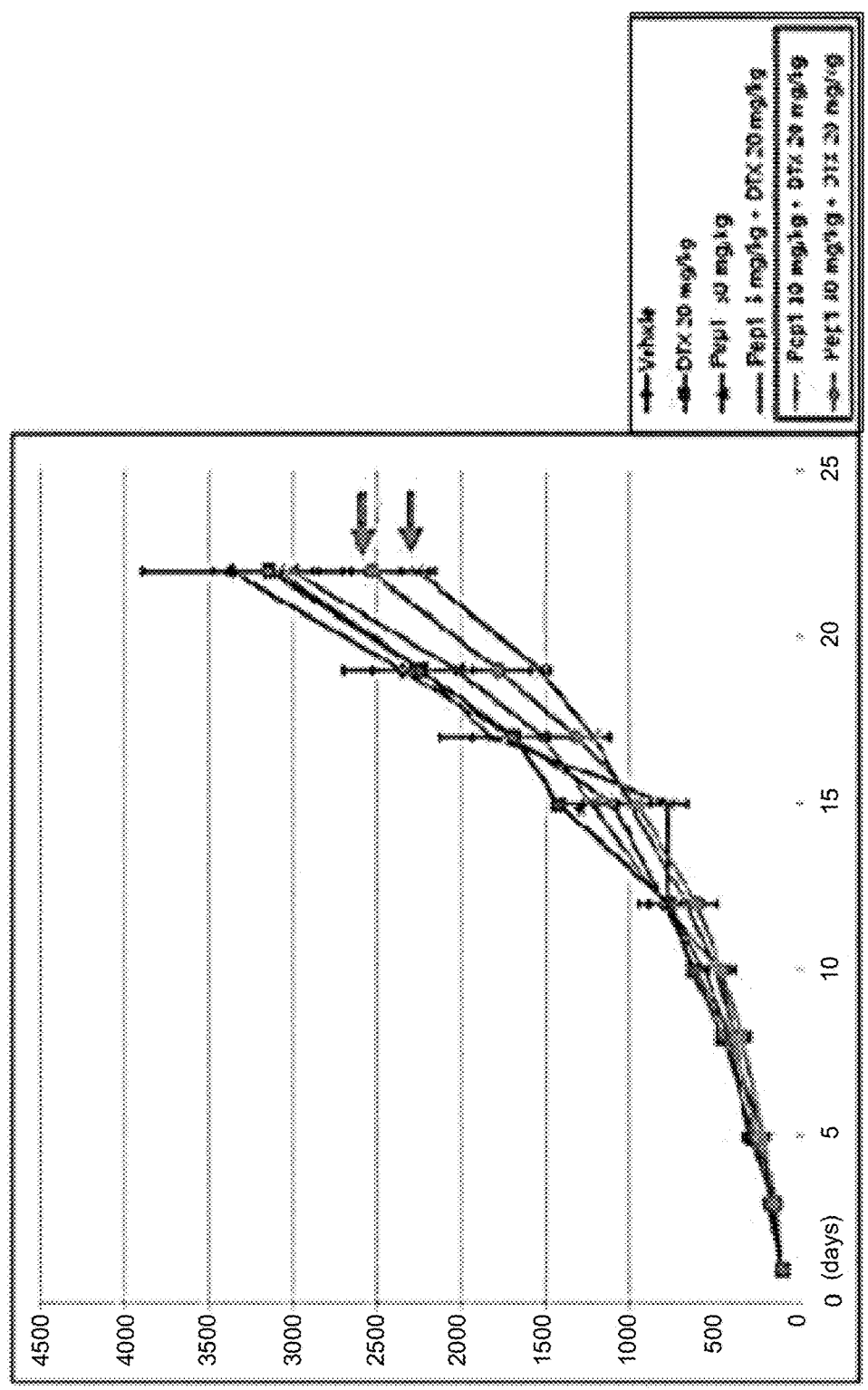
FIG. 5 shows a graph of tumor volume over time of test groups to which various concentrations of Pep1 and docetaxel are co-administered, to evaluate effects of the co-administration of Pep1 and docetaxel in an LNCaP cell xenograft model.

According to test results associated with the co-administration of Pep1 and docetaxel, it was confirmed that when docetaxel was co-administered with Pep1, significant inhibition effects was obtained. In the case of the test group in which 10 mg/kg of Pep1 was co-administered with 20 mg/kg of docetaxel, at a final evaluation phase, distinct cancer growth inhibition effects were obtained (see FIG. 5, the Y axis of FIG. 5 indicates a tumor volume (mm$^3$)). That is, even the co-administration of Pep1 and docetaxel has lead significant cancer growth inhibition effects on the LNCaP cell in an animal model.

Example 4

Measuring Body Weight of LNCaP Cell-Xenografted Model when Pep1 was Administered Thereto The body weight of each of the test groups 1) of 7) described in Example 3 was measured with respect to the tumor cell growth in LNCaP xenograft model.

Figure 6:
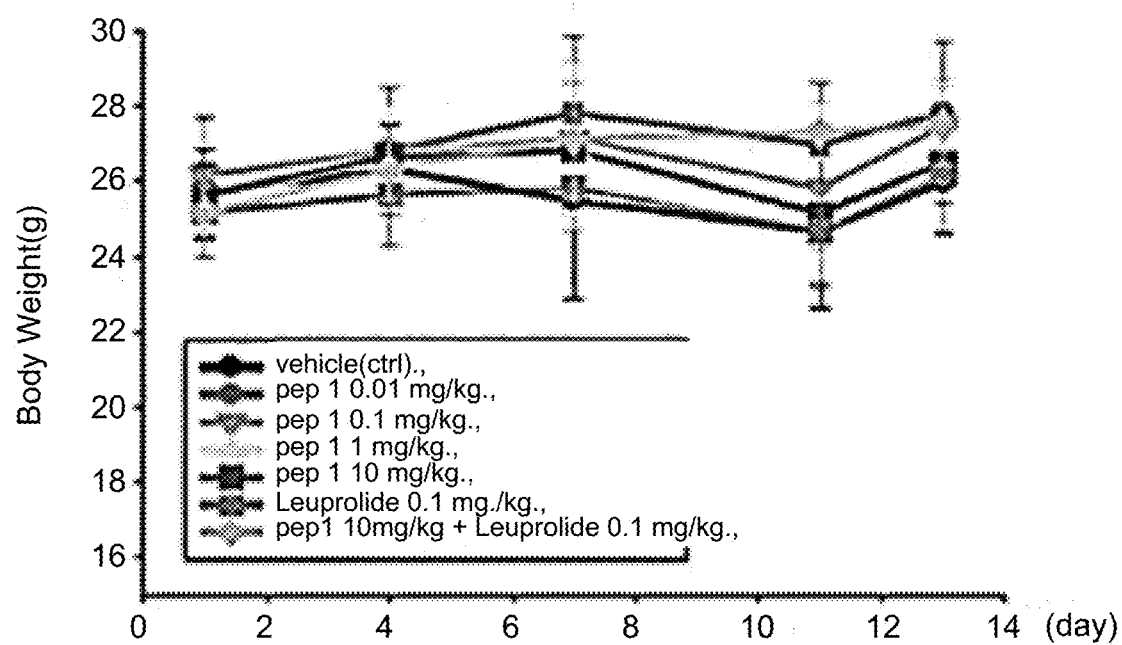
FIG. 6 shows a graph of body weight over time of test groups to which various concentrations of Pep1 and leuprolide acetate are administered separately or together, to evaluate safety of Pep1 and the co-administration of Pep1 and leuprolide acetate in an LNCaP cell xenograft model.

The obtained assay results of the test groups show that the administered Pep1 is safe in vivo since there was no significant difference in the body weight among the control (vehicle. test group 1)), the test groups 6) and 7) in which leuprolide acetate was administered alone or together with Pep1, and the test groups 2) to 5) having different concentrations of Pep1 (see FIG. 6).

Example 5: Evaluating cancer cell migration inhibition effects of Pep1 in LNCaP cell line model The effects of Pep1 on cancer cell migration were evaluated by trans-well assay.

The cancer cell migration was evaluated by using the reagents and materials and the cell line incubation method which are described in connection with Example 1. A migration assay method used for this experiment is as follows.

The LNCaP cell line was incubated on a 6-well plate overnight, and then treated with various concentrations of Pep1 (0, 1, 10, 30 μM) and incubated for 24 hours. Thereafter, the resultant LNCaP cell line was seeded at the cell population of 1×10⁴/well on a trans-well plate. Three hours after, the upper compartment of each well was removed, and cells that had migrated downwards were immobilized, stained, and quantified.

A separate experiment was further performed to identify cell migration when Pep1 was co-administered with docetaxel. The LNCaP cell line was incubated on a 6-well plate overnight, and then, treated with various concentrations of Pep1(0, 1, 3, 10, and 30 μM) and incubated for 24 hours. Additionally, the cell line was incubated in a growth medium containing docetaxel (3 nM) for 48 hours, and then, seeded on a trans-well plate at a cell population of 1×10⁴/well. Three hours after, the upper compartment of each well was removed, and cells that had migrated downwards were immobilized, stained, and quantified.

To analyze test results, averages of test groups were verified by performing student's t-test. The reference of the statistical significance was set at p<0.05(*) or p<0.01(**).

Figure 7:
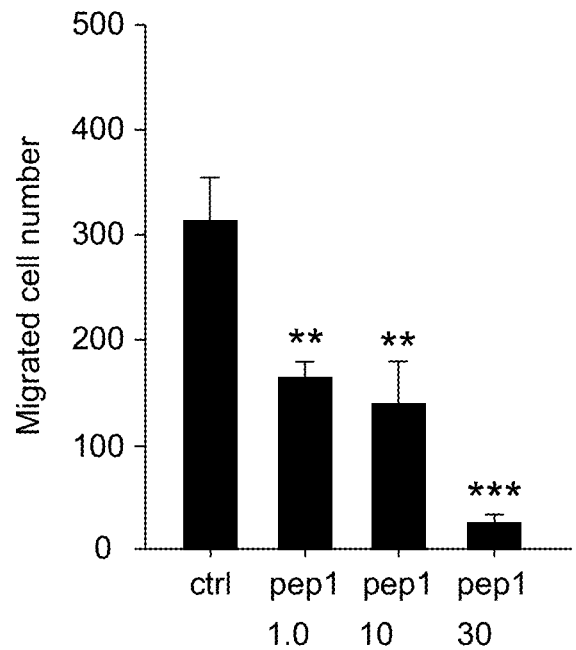
FIG. 7 shows a graph of a migrated cell number when various concentrations of Pep1 are administered to cells, to evaluate migration inhibition effects of Pep1 on an LNCaP identified by transwell migration assay.
Figure 8:
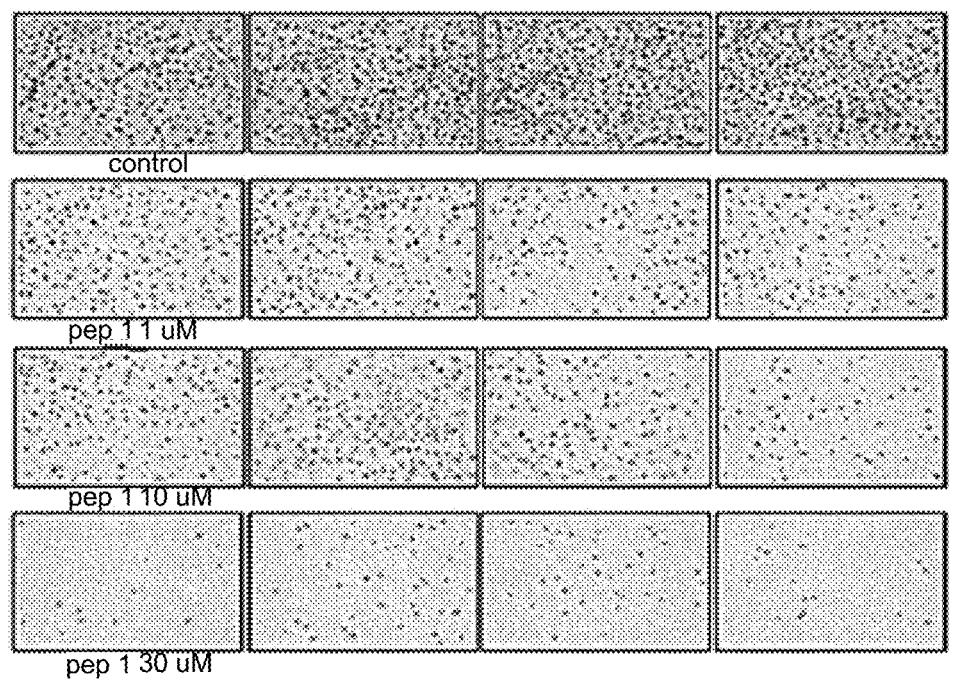
FIG. 8 shows images of cells to which various concentrations of Pep1 is administered, to evaluate migration inhibition effects of Pep1 on an LNCaP identified by transwell migration assay.
Figure 9:
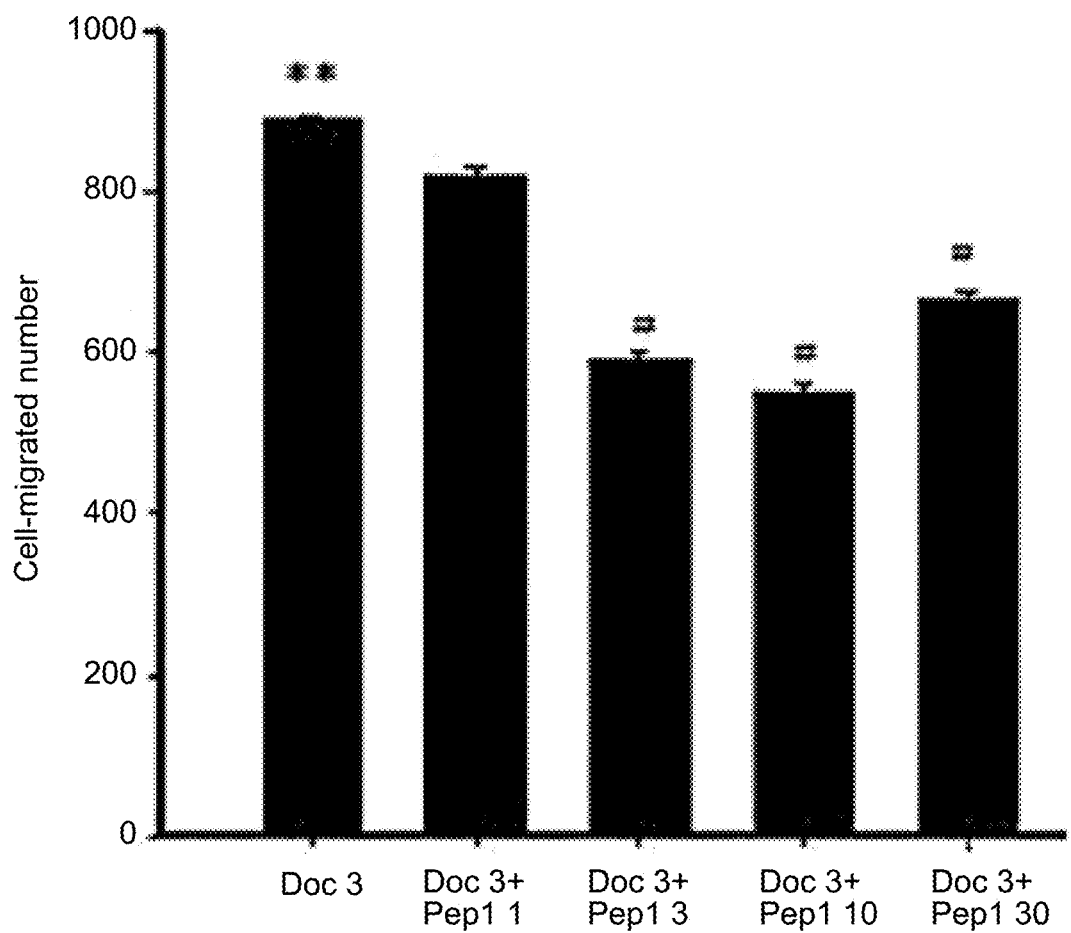
FIG. 9 shows a graph of a migrated cell number when various concentrations of Pep1 and docetaxel are co-administered to cells, to evaluate migration inhibition effects of the co-administration of Pep1 and docetaxel in an LNCaP identified by transwell migration assay.
Figure 10:
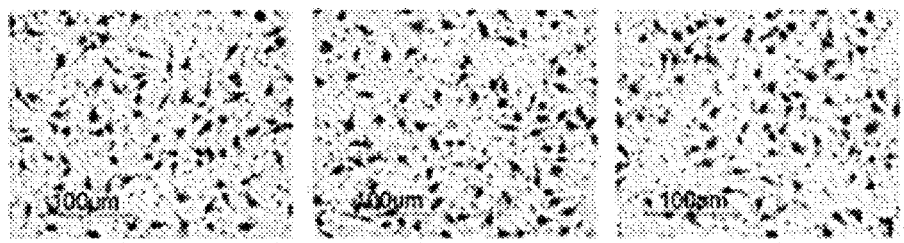
FIGS. 10 to 14 show images of cells to which various concentrations of Pep1 and docetaxel are co-administrated, to evaluate migration inhibition effects of the co-administration of Pep1 and docetaxel in an LNCaP identified by transwell migration assay.
Figure 11:
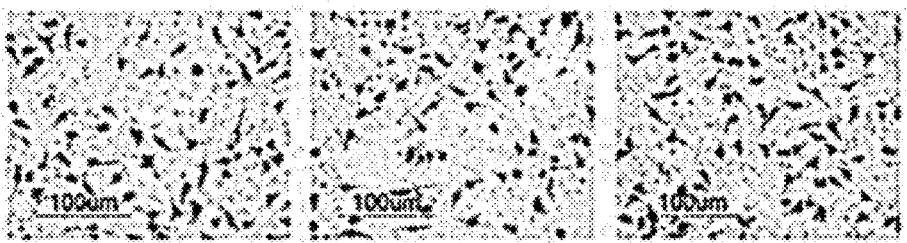
Figure 12:
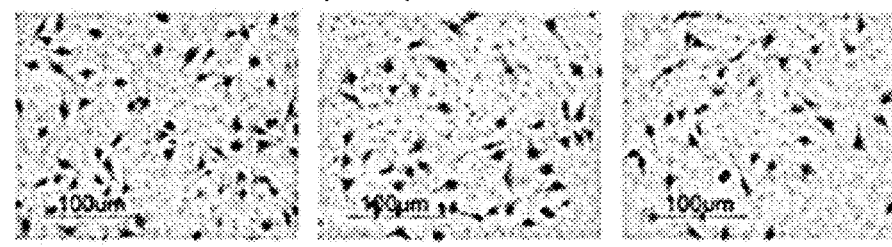
Figure 13:
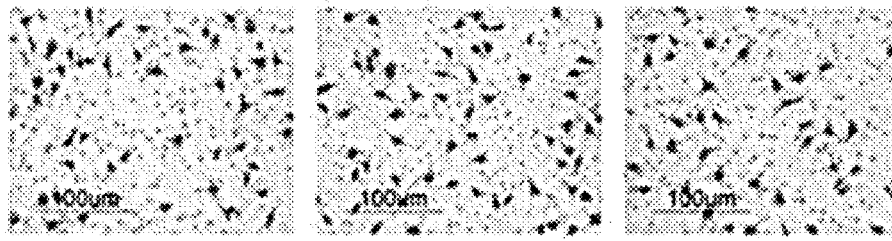
Figure 14:
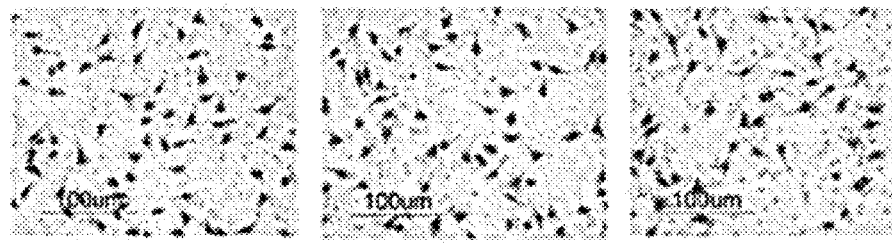

According to results of the trans-well assay performed as described above, in the case of the Pep1-free medium (0 μM, control), the cancer cell migration was increased, but in the case of the medium treated with Pep1 (1 μM, 10 μM, and 30 μM), the cancer cell migration was statistically significantly inhibited (see FIGS. 7 and 8). Referring to FIGS. 7 and 8, the control refers to a test group that is grafted with LNCaP and is not treated with Pep1.

Further experiments were performed by co-administered with docetaxel. In the case of the medium containing docetaxel (3 nM), the cancer cell migration was increased, but when the medium containing docetaxel (3 nM) was treated with Pep1 (3 μM, 10 μM, and 30 μM), the cancer cell migration was statistically significantly inhibited. (see FIGS. 9 to 14).

Example 6

Measuring mRNA Expression of Cancer Cells Migration Markers (MMP9, MMP2) when LNCaP Cell Line Model was Administered with Pep1

Figure 15:
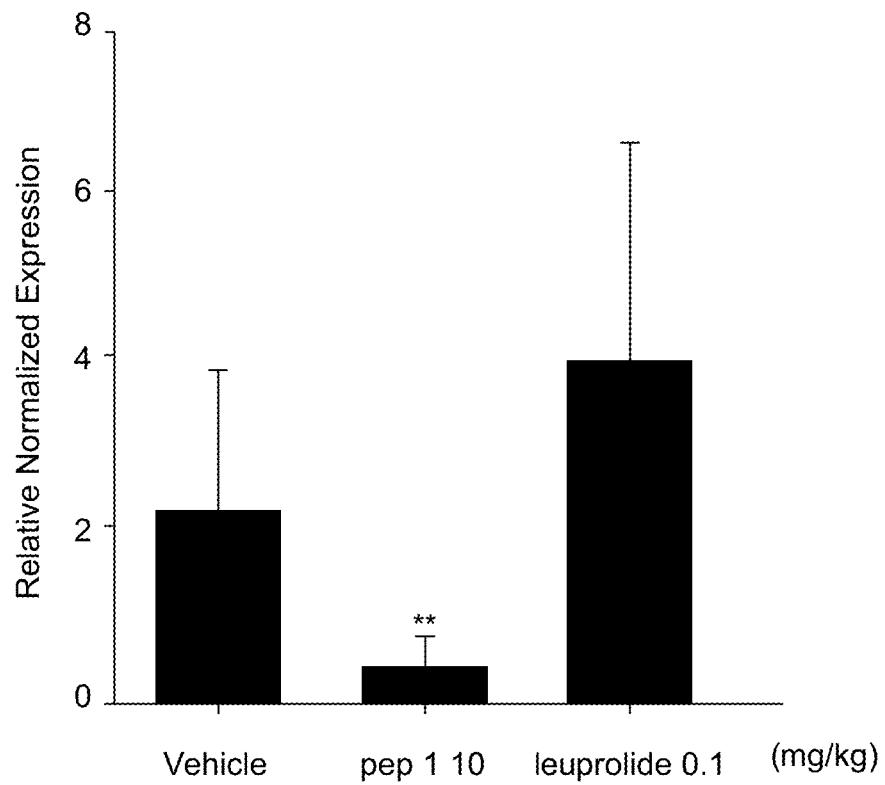
FIG. 15 shows a graph of an expression level of MMP9, which is an mRNA marker associated with the migration of cancer cells in an LNCaP cell xenograft model, when 10 mg/kg of Pep1 and 0.1 mg/kg of leuprolide acetate are administered to test groups and a control.
Figure 16:
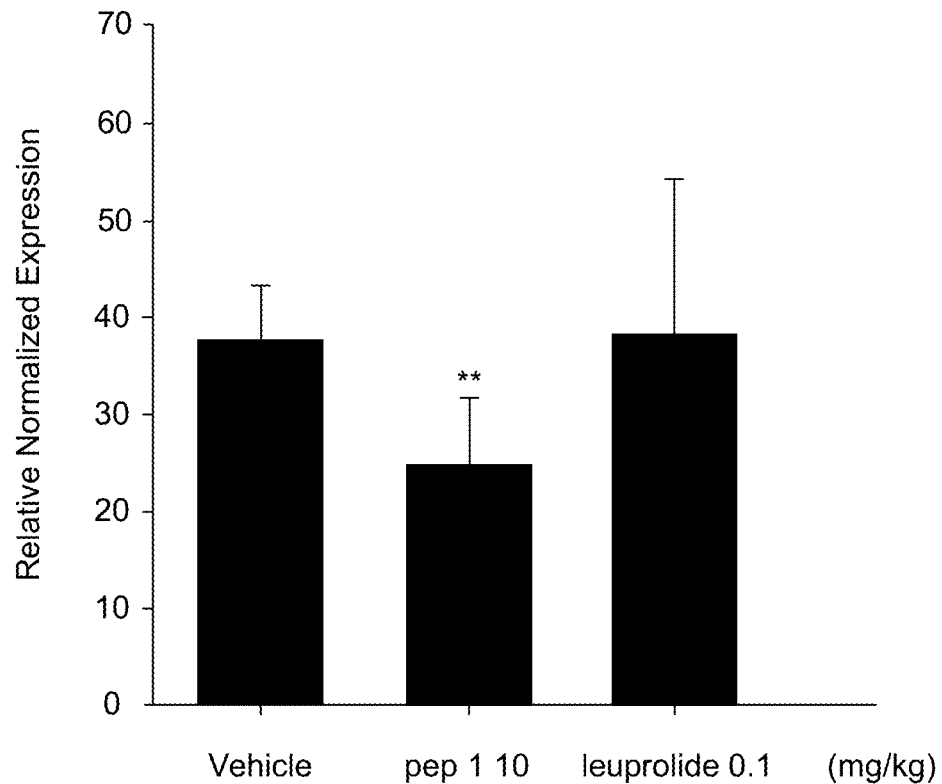
FIG. 16 shows a graph of an expression level of MMP2, which is an mRNA marker associated with the migration of cancer cells in an LNCaP cell xenograft model, 10 mg/kg of Pep1, and 0.1 mg/kg of leuprolide acetate are administered to test groups and a control.

Relative expression levels in tissues xenografted with LNCaP were evaluated to identify the expression of MMP9 (Matrix Metalloproteinase-9) and MMP2 (Matrix Metalloproteinase-2), which are mRNA markers and show cancer cell migration (see FIGS. 15 and 16).

Test groups 14) to 16) were grafted with LNCaP cell. This experiment was performed by using the reagents and materials and the cell line incubation method which are described in connection with Example 1.

The LNCaP cell line was a human prostate cancer metastasis cell, and obtained from American Type Cell Culture (ATCC, Rockville, MD). The LNCaP cell line was incubated in a RPMI containing 10% FBS, 50 U/ml penicillin, and 50 μg/ml streptomycin until the cell population was 1 to $2\times10^6$/ml in a 5% $CO_2$ incubator in which the temperature was maintained at 37° C.

Test animals: 3 test groups were grafted with the LNCaP cell. The test groups consisted of 5-week BALB/c-nu mice (obtained from Central Lab. Animal Inc., Seoul, Korea). For each group, 6 mice and extra 5 mice were stabilized for 1 week. Each mouse was grafted at its side with the LNCaP cell having the cell population of $1*10^7$ cells suspended in 100 μl PBS, and observed for 2 weeks. From among the total of 11 mice, 5 mice that had not developed tumor or that had had a significantly small tumor were not used. The 3 test groups, each consisting of the remaining 6 mice, were treated according to the conditions as below for 20 days.

Following the grafting, Pep1 and leuprolide acetate (positive control) were administered to the 2 test groups by subcutaneous injection every day.

14) LNCaP-grafted control (vehicle)
15) LNCaP graft+10 mg/kg of Pep1
16) LNCaP graft+0.1 mg/kg of leuprolide acetate To analyze test results, averages of test groups were verified by performing student's t-test. The reference of the statistical significance was set at p<0.05(*) or p<0.01(**).

From tumor tissues harvested from the 3 test groups, RNA was extracted, and RT-PCR was performed thereon by using primers of MMP9 and MMP2. Each sample obtained by RT-PCR amplification was allowed to flow through 2D gel by electrophoresis, and then, fluorescence-stained to measure the level of expression. The PCR assay of mRNA was performed by using a well known method.

The relative expression level of MMP9 was evaluated with reference to the expression level of the control (vehicle) being set to 2 (see FIG. 15), and the relative expression level of MMP2 was evaluated with reference to the expression level of the control (vehicle) being set to 38 (see FIG. 16).

MMP9 and MMP2 showed low expression levels in tumor tissues administered with Pep1 compared to the control (vehicle) and the positive control (Leuprolide). This result shows that Pep1 is effective for the decrease in cancer cells migration in cancer tissues.

In Example 2, it was confirmed that Pep1 showed prostate cancer cell line growth inhibition effects when Pep1 was administered alone or together with conventional anti-cancer drugs. In Examples 3 and 5, it was confirmed that Pep1 was effective for the decrease in the volume of cancer cells in an animal model grafted with the prostate cancer cell line (Example 3) and was effective for the inhibition of the migration of prostate cancer cells (Example 5). In Example 6, it was confirmed that Pep1 was effective for the inhibition of the expression of an mRNA marker associated with cancer cell migration that shows metastasis of prostate cancer. In Example 4, it was confirmed that Pep1 had safety when administered since the body weight was not significantly changed when administered. In conclusion, it is seen that Pep1 is effective for inhibiting the growth and metastasis of prostate cancer and has safety, and accordingly, Pep1 may be included in a prostate cancer growth inhibition agent or a prostate cancer metastasis inhibition agent. Thus, Pep1 is likely to be used in a prostate cancer drug.

What is claimed is:

1. A method of treating hormone-tolerant prostate cancer in a patient in need thereof comprising administering to the patient the isolated peptide of SEQ ID NO: 1 and an anti-cancer drug selected from docetaxel or leuprolide acetate, wherein tumor volume is decreased upon co-administration of the isolated peptide of SEQ ID NO: 1 with docetaxel or leuprolide acetate compared to administration of docetaxel or leuprolide acetate alone.

2. The method according to claim 1, wherein the patient has at least one of eotaxin and MIP1α at a serum concentration of at least 10% higher than the average serum concentration in prostate cancer patients.

3. The method according to claim 1, wherein the peptide is administered at a daily dose of 0.1 ng/kg to 10 mg/kg.

4. The method according to claim 1, wherein the peptide is administered at a daily dose of 1 μg/kg to 100 μg/kg.

5. The method according to claim 1, wherein the peptide is administered three times per week during the first week, followed by once per week during the second, third, fourth, and sixth week, and followed by once every four weeks thereafter.

6. The method according to claim 1, wherein docetaxel is administered in a range of 60 mg/m$^2$ to 400 mg/m$^2$.

7. The method according to claim 1, wherein docetaxel is intravenously administered every three weeks in a range of 60 mg/m$^2$ to 100 mg/m$^2$ during one hour.

8. A method of treating hormone-tolerant prostate cancer in a patient in need thereof comprising administering to the patient a composition comprising the isolated peptide of SEQ ID NO: 1 and an anti-cancer drug selected from docetaxel or leuprolide acetate, wherein tumor volume is decreased upon co-administration of a composition comprising the isolated peptide of SEQ ID NO: 1 with docetaxel or leuprolide acetate compared to administration of docetaxel or leuprolide acetate alone.

9. The method according to claim 8, wherein the patient has at least one of eotaxin and MIP1α at a serum concentration of at least 10% higher compared to their average serum concentration in prostate cancer patients.

10. The method according to claim 8, wherein the composition is administered through an oral, rectal, transdermal, intravenous, intramuscular, intraperitoneal, in the bone marrow, epidural, or subcutaneous route.

11. The method of claim 8, wherein the composition comprises 0.01 g/L to 1 kg/L of the isolated peptide.

12. The method of claim 8, wherein the peptide is administered at a daily dose of 0.1 ng/kg to 10 mg/kg.

13. The method according to claim 8, wherein the peptide is administered at a daily dose of 1 μg/kg to 100 μg/kg.

14. The method according to claim 8, wherein the composition is administered three times per week during the first week, followed by once per week during the second, third, fourth, and sixth week, and followed by once every four weeks thereafter.

15. The method according to claim 8, wherein docetaxel is administered in a range of 60 mg/m$^2$ to 400 mg/m$^2$.

16. The method according to claim 8, wherein docetaxel is intravenously administered every three weeks in a range of 60 mg/m$^2$ to 100 mg/m$^2$ during one hour.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
```

<213> ORGANISM: Homo sapiens

<400> SEQUENCE: 2

| | | | | | | | | | | | | | | |
|---|---|---|---|---|---|---|---|---|---|---|---|---|---|---|
| Met | Pro | Arg | Ala | Pro | Arg | Cys | Arg | Ala | Val | Arg | Ser | Leu | Leu | Ser |
| 1 | | | | 5 | | | | | 10 | | | | | 15 |
| His | Tyr | Arg | Glu | Val | Leu | Pro | Leu | Ala | Thr | Phe | Val | Arg | Leu | Gly |
| | | | 20 | | | | | 25 | | | | | 30 | |
| Pro | Gln | Gly | Trp | Arg | Leu | Val | Gln | Arg | Gly | Asp | Pro | Ala | Ala | Phe | Arg |
| | | 35 | | | | | 40 | | | | | 45 | | | |
| Ala | Leu | Val | Ala | Gln | Cys | Leu | Val | Cys | Val | Pro | Trp | Asp | Ala | Arg | Pro |
| 50 | | | | | 55 | | | | | 60 | | | | | |
| Pro | Pro | Ala | Ala | Pro | Ser | Phe | Arg | Gln | Val | Ser | Cys | Leu | Lys | Glu | Leu |
| 65 | | | | | 70 | | | | | 75 | | | | | 80 |
| Val | Ala | Arg | Val | Leu | Gln | Arg | Leu | Cys | Glu | Arg | Gly | Ala | Lys | Asn | Val |
| | | | | 85 | | | | | 90 | | | | | 95 | |
| Leu | Ala | Phe | Gly | Phe | Ala | Leu | Leu | Asp | Gly | Ala | Arg | Gly | Gly | Pro | Pro |
| | | | 100 | | | | | 105 | | | | | 110 | | |
| Glu | Ala | Phe | Thr | Thr | Ser | Val | Arg | Ser | Tyr | Leu | Pro | Asn | Thr | Val | Thr |
| | | | | 115 | | | | | 120 | | | | | 125 | |
| Asp | Ala | Leu | Arg | Gly | Ser | Gly | Ala | Trp | Gly | Leu | Leu | Arg | Arg | Val |
| 130 | | | | | 135 | | | | | 140 | | | | | |
| Gly | Asp | Val | Leu | Val | His | Leu | Leu | Ala | Arg | Cys | Ala | Leu | Phe | Val |
| 145 | | | | 150 | | | | | 155 | | | | | 160 |
| Leu | Val | Ala | Pro | Ser | Cys | Ala | Tyr | Gln | Val | Cys | Gly | Pro | Pro | Leu | Tyr |
| | | | 165 | | | | | 170 | | | | | 175 | | |
| Gln | Leu | Gly | Ala | Ala | Thr | Gln | Ala | Arg | Pro | Pro | Pro | His | Ala | Ser | Gly |
| | | | 180 | | | | | 185 | | | | | 190 | | |
| Pro | Arg | Arg | Arg | Leu | Gly | Cys | Glu | Arg | Ala | Trp | Asn | His | Ser | Val | Arg |
| | | 195 | | | | | 200 | | | | | 205 | | | |
| Glu | Ala | Gly | Val | Pro | Leu | Gly | Leu | Pro | Ala | Pro | Gly | Ala | Arg | Arg |
| 210 | | | | | 215 | | | | | 220 | | | | | |
| Gly | Gly | Ser | Ala | Ser | Arg | Ser | Leu | Pro | Leu | Pro | Lys | Arg | Pro | Arg | Arg |
| 225 | | | | | 230 | | | | | 235 | | | | | 240 |
| Gly | Ala | Ala | Pro | Glu | Pro | Glu | Arg | Thr | Pro | Val | Gly | Gln | Gly | Ser | Trp |
| | | | | 245 | | | | | 250 | | | | | 255 | |
| Ala | His | Pro | Gly | Arg | Thr | Arg | Gly | Pro | Ser | Asp | Arg | Gly | Phe | Cys | Val |
| | | | 260 | | | | | 265 | | | | | 270 | | |
| Val | Ser | Pro | Ala | Arg | Pro | Ala | Glu | Glu | Ala | Thr | Ser | Leu | Glu | Gly | Ala |
| | | 275 | | | | | 280 | | | | | 285 | | | |
| Leu | Ser | Gly | Thr | Arg | His | Ser | His | Pro | Ser | Val | Gly | Arg | Gln | His | His |
| | 290 | | | | | 295 | | | | | 300 | | | | |
| Ala | Gly | Pro | Pro | Ser | Thr | Ser | Arg | Pro | Pro | Arg | Pro | Trp | Asp | Thr | Pro |
| 305 | | | | | 310 | | | | | 315 | | | | | 320 |
| Cys | Pro | Pro | Val | Tyr | Ala | Glu | Thr | Lys | His | Phe | Leu | Tyr | Ser | Ser | Gly |
| | | | | 325 | | | | | 330 | | | | | 335 | |
| Asp | Lys | Glu | Gln | Leu | Arg | Pro | Ser | Phe | Leu | Leu | Ser | Ser | Leu | Arg | Pro |
| | | | | 340 | | | | | 345 | | | | | 350 | |
| Ser | Leu | Thr | Gly | Ala | Arg | Arg | Leu | Val | Glu | Thr | Ile | Phe | Leu | Gly | Ser |
| | | | 355 | | | | | 360 | | | | | 365 | | |
| Arg | Pro | Trp | Met | Pro | Gly | Thr | Pro | Arg | Arg | Leu | Pro | Arg | Leu | Pro | Gln |
| | | 370 | | | | | 375 | | | | | 380 | | | |
| Arg | Tyr | Trp | Gln | Met | Arg | Pro | Leu | Phe | Leu | Glu | Leu | Leu | Gly | Asn | His |
| 385 | | | | | 390 | | | | | 395 | | | | | 400 |

-continued

```
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Leu Val Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Glu Ile Leu Ala Lys Phe
    530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
```

-continued

```
                820                 825                 830
Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130
```